United States Patent [19]

Cooper et al.

[11] Patent Number: 5,296,593
[45] Date of Patent: Mar. 22, 1994

[54] COMPLEXES OF THIOETHERS

[75] Inventors: Stephen R. Cooper, Oxford, England; Heinz-Josef Kueppers, Muelheim an der Ruhr, Fed. Rep. of Germany; Philip Blower, Canterbury, England

[73] Assignee: Isis Innovation Limited, Oxford, England

[21] Appl. No.: 982,698

[22] Filed: Nov. 30, 1992

[30] Foreign Application Priority Data

Mar. 29, 1990 [GB] United Kingdom ............... 9007039

[51] Int. Cl.$^5$ ............................................. C07F 13/00
[52] U.S. Cl. .............................................. 534/14
[58] Field of Search ................. 534/14; 424/1.1; 549/11; 568/57

[56] References Cited

U.S. PATENT DOCUMENTS 4,925,925  5/1990  Deutsch ..................... 424/1.1 X Primary Examiner—Gary Geist
Attorney, Agent, or Firm—Nixon & Vanderhye

[57] ABSTRACT

Technetium-99m complexes of crown thioethers having 3 to 6 donor sulphur atoms joined into a macrocyclic ring by C2 or C3 groups, for example 1,4,7-trithiacyclononane (9S3); and of tripodal ligands having more than 3 donor sulphur atoms joined by C2 or C3 groups, for example, 1,1,1-tris(((2-methylthio)ethylthio)methyl)ethane.

7 Claims, 1 Drawing Sheet

COMPLEXES OF THIOETHERS

This is a continuation of PCT application No. PCT/GB91/00482, filed Mar. 28, 1991.

This invention concerns technetium complexes of thioethers. In one embodiment, the thioether is a crown thioether having three to six donor sulphur atoms joined into a macrocyclic ring by C2 or C3 groups.

In another embodiment, there is used a tripodal ligand having more than three donor sulphur atoms joined by C2 or C3 groups.

Technetium-99m is a γ-emitter having a half life of 6 hours, which is very widely used for body imaging. Complexes according to the invention in which technetium is $Tc^{99m}$ are expected to have interesting biodistribution properties and to constitute useful body imaging agents.

Tripodal ligands are typically 1,1,1-substituted ethanes, in which each of the three substituents contains at least one sulphur atom. The three substituent groups may be different but are generally the same, and contain between them more than three sulphur atoms.

Figure 1:
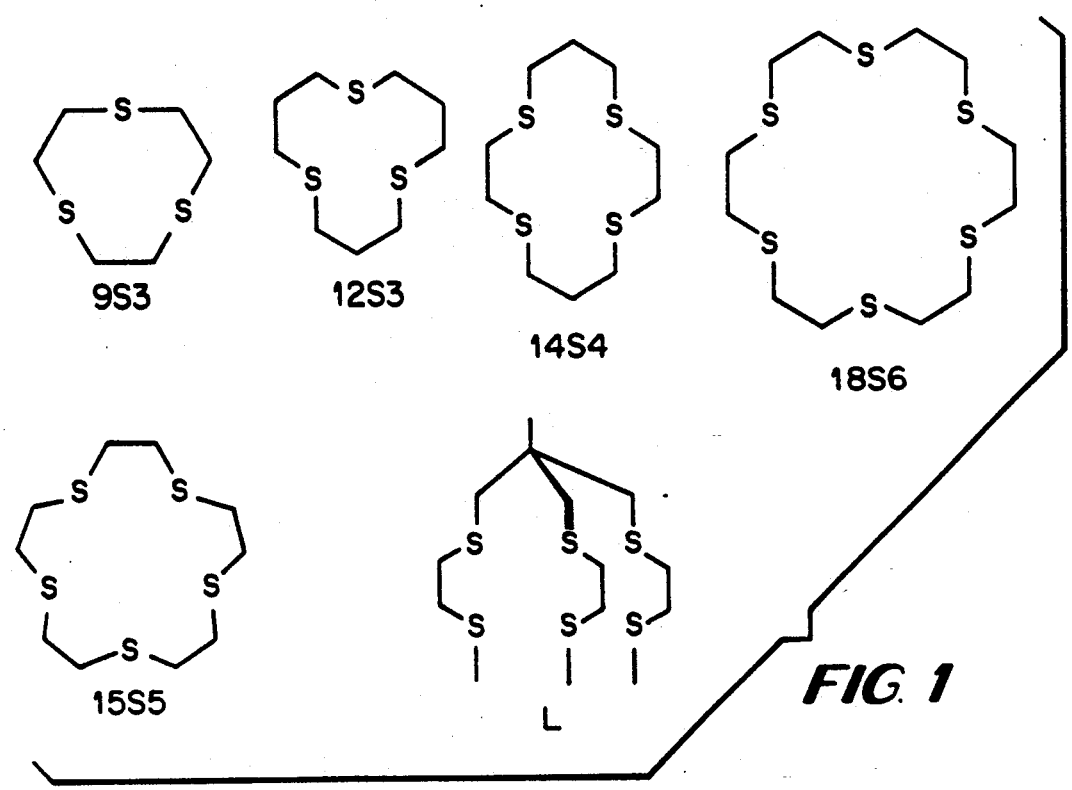

Examples of crown thioethers and tripodal ligands are shown in FIG. 1.

In the crown thioether designations, the first figure represents the number of atoms, and the last figure the number of sulphur atoms, in the macrocyclic ring. Thus:

9S3 = 1,4,7-trithiacyclononane;
12S3 = 1,5,9-trithiacyclocododecane;
14S4 = 1,4,8,11-tetrathiacyclotetradecane;
15S5 = 1,4,7,10,13-pentathiacyclopentadecane;
18S6 = 1,4,7,10,13,16-hexathiacyclooctadecane;
L = 1,1,1-tris(((2-methylthio)ethyl)thio)methyl)ethane.

The complex may comprise, associated with each Tc atom: one or two thioether ligands; 0, 1, 2, or 3 oxo groups; and 0, 1, 2 or 3 halide or pseudohalide groups (e.g. F, Cl, Br, I or NCS). The following diagram shows the Tc thioether complexes that are chemically plausible. Parentheses enclose the charges of species less likely to exist. X denotes halide or pseudohalide.

these involve reaction of thioether dithiols with oligo(thioether) dichlorides in dimethylformamide containing $Cs_2CO_3$ as base. Syntheses of 9S3 (Equation 1), 18S6 (Equations 2a–2c), and supertripodal ligand L (Equations 3a–b) are shown below.

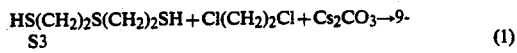  (1)

  (2a)

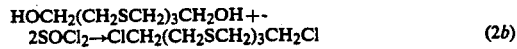  (2b)

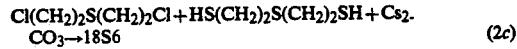  (2c)

  (3a)

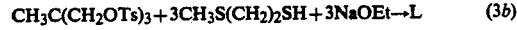  (3b)

Crown thioethers were first prepared over fifty years ago, but their coordination chemistry was not examined until the early 1960s, and most of their coordination chemistry has been investigated in the last ten years. For example, the ligand 9S3 was prepared in 1977 and its coordination dates back only to 1982. In that time crown thioether complexes of a number of transition metals, including particularly Ru (with 14S4 and 9S3) have been prepared.

In the light of this earlier work, it was unclear what oxidation state of Tc would result in any complexes that might be formed when the ligand was reacted with pertechnetate, and the biodistribution properties of any resulting complexes were also unclear.

By analogy with earlier work, the crown thioethers should form Tc chelates that differ in redox potential (for the hexakis(thioether) series $[Tc(L)_2]^{2+}$, L=9S3, 12S3, 18S6) and in coordination number (for $[Tc(14S4)X_m]^{n+}$, where m can be 1 or 2, and $[Tc(15S5)X]^{n+}$). Variation in redox potential provides an important means of tuning the charge on the cation, and thereby influencing its biodistribution. For example, a chelate for which Tc(III/II) potential falls within

| | Oxidation State: | Tc(I) | Tc(II) | Tc(III) | Tc(IV) | Tc(V) | Tc(VI) | Tc(VII) |
|---|---|---|---|---|---|---|---|---|
| $TcS_6$ | $[Tc(9S3)_2]^{n+}$ | n = 1+ | 2+ | 3+ | | | | |
| | $[Tc(12S3)_2]^{n+}$ | 1+ | 2+ | 3+ | | | | |
| | $[Tc(18S6)]^{n+}$ | 1+ | 2+ | 3+ | | | | |
| | $[Tc(L)]^{n+}$ | 1+ | 2+ | 3+ | | | | |
| | $[Tc(14S4)]^{n+}$ | | (2+) | (3+) | | | | |
| $TcOX_2S_3$ | $[TcOX_2(9S3)]^{n+}$ | | | (1−) | 0 | 1+ | 2+ | 3+ |
| | $[TcOX_2(12S3)]^{n+}$ | | | (1−) | 0 | 1+ | 2+ | 3+ |
| $TcOS_n$ | $[TcO(14S4)]^{n+}$ | | | 1+ | 2+ | 3+ | 4+ | 5+ |
| | $[TcO(15S5)]^{n+}$ | | | (1+) | 2+ | 3+ | 4+ | 5+ |
| $TcO_2XS_3$ | $[TcO_2X(9S3)]^{n+}$ | | | (−2) | 1− | 0 | 1+ | 2+ |
| | $[TcO_2X(12S3)]^{n+}$ | | | (−2) | 1− | 0 | 1+ | 2+ |
| | $TcO_2(14S4)]^{n+}$ | | (−2) | 1− | 0 | 1+ | 2+ | |
| $TcO_3S_3$ | $[TcO_3(9S3)]^{n+}$ | | | | | (1−) | (0) | 1+ |
| | $[TcO_3(12S3)]^{n+}$ | | | | | (1−) | (0) | 1+ |

Synthesis of Ligands

Ligand L was synthesized for the first time in the inorganic Chemistry Laboratory at Oxford University in 1986. This and subsequent work revealed the efficacy of L as a ligand for Co(II) and Ni(II). Subsequent work has shown that it also strongly binds Ru(II) to produce the hexacoordinated $[Ru(L)]^{2+}$ cation.[3]

Crown thioethers ligands were prepared by routes that have now appeared in the literature. In general the physiological range would not localise cleanly in one tissue. Suitable choice of a different ligand could be used to shift the potential out of the physiological range and thereby obviate this problem.

The availability of coordination sites on the Tc ion also influences biodistriution. Easily displaced X ligands (as opposed to the crown thioether, which is more difficult to displace) allows the biological milieu to interact with Tc chelates (e.g., those used for bone imaging).

This interaction (with proteins thiolate groups, for example) can strongly influence biodistribution. The crown thioethers have been chosen either to saturate the Tc coordination sphere (9S3, 12S3, 18S6) or to not to do so (14S4, 15S5) in order to examine both types of behaviour.

Synthesis and Characterisation of the Tc Chelates

Reaction of n-Bu$_4$NTcO$_4$ (85 mg, 0.21 mmol) with the crown thioether 9S3 (160 mg, 0.9 mmol) in MeCN (5 ml) and HBF$_4$ (0.4 mL of a 54% solution in Et$_2$O) added to give a dark brown solution. After stirring for 1 h a brown microcrystalline precipitate formed, which was washed with Et$_2$O to give the product (115 mg, 79%). Elemental analysis indicates the formula [Tc(9S3)$_2$](BF$_4$).2H$_2$O.½MeCN, a previously unreported compound. (Anal. Calc. (found) for C$_{13}$H$_{29.5}$N$_{0.5}$O$_2$S$_6$B$_2$F$_8$Tc: C 22.76 (22.63), H 5.16 (4.34), N 0.99 (1.01).

Addition of saturated aqueous solution of NH$_4$PF$_6$ to the BF$_4^-$ salt dissolved in 5 mL H$_2$O precipitated a golden brown solid that was filtered, washed with H$_2$O and Et$_2$O and dried in air. Elemental analysis indicates the formula [Tc(9S3)$_2$](PF$_6$).H$_2$O, also a previously unreported compound. (Anal. calc. (found) for C$_{12}$H$_{26}$OS$_6$P$_2$F$_{12}$Tc: C 18.75 (18.78); H 3.12 (3.41).

Crystals formed upon slow diffusion of Et$_2$O into solutions of the BF$_4^-$ or PF$_6^-$ salts in CH$_3$CN or CH$_3$NO$_2$. During the crystallisation sometimes became pale red, which may correspond to a product resulting from either solvolysis (particularly hydrolysis by adventitious water) or slow oxidation by air.

Electrochemistry

Electrochemical characterisation of [Tc(9S3)$_2$]$^{2+}$ by cyclic voltammetry (MeCN, Pt electrode, 0.1 M Bu$_4$NPF$_6$ electrolyte) shows a quasi-reversible wave (probably corresponding to the Tc (II/I) couple) at +0.05V vs the saturated calomel electrode (SCE; −0.38V vs ferrocenium/ferrocene (Fc$^+$/Fc), +0.02 vs standard hydrogen electrode, (SHE). It also shows an irreversible one-electron oxidation at +1.3 V vs SCE (+0.87 V vs Fc$^+$/Fc, +1.27 V vs SHE).

Another redox couple yields an irreversible reduction at −1.6 V vs SCE (−2.03 V vs Fc$^+$.Fc, −1.63 V vs. SHE). Owing to its much smaller peak current than that of the waves described above, this redox process probably results from either an impurity or from a reaction product of [Tc(9S3)$_2$]$^{2+}$ under the experimental conditions.

In addition, a quasi-reversible process appears at −0.66V vs SCE (−1.09 V vs Fc$^+$/Fc, −0.69 V vs SHE). On the first scan (100 mV/s) this wave has a current one-fourth that of the wave at +0.05V vs SCE. During subsequent scans the current associated with this wave at −0.66 V vs SCE grew at the expense of that at +0.05 V vs SCE; by the tenth scan the system reaches either an equilibrium or a steady state. These results suggest that upon reduction of [Tc(9S3)$_2$]$^{2+}$ to [Tc(9S3)$_2$]$^+$ (the process at +0.05 V) the electrogenerated [Tc(9S3)$_2$]$^+$ reacts (perhaps) with CH$_3$CN to give a product that is redox-active in its own right (and which gives rise to the wave at −0.66 V).

Cyclic voltammetry in aqueous solution employed 0.1 M NaCl as supporting electrolyte; other conditions were as described above. Two quasi-reversible redox processes occur, one at −0.20 V vs SCE (+0.02 V vs. NHE) and another at −0.60 V vs. SCE (−0.37 V vs. NHE). The peak current of the second wave depends on the number of scans. On successive scans it grew to an equilibrium or steady state value about half that of the wave at −0.20 V.

Supertripodal Ligand L

Parallel synthetic procedures with the supertripodal compound L yielded evidence for the analogous Tc(II) complex. Under the conditions described above L reacts with TcO$_4^-$ to yield a solution identical in appearance with that of the 9S3 homologue. Consequently it is formulated as [Tc(L)]$^{2+}$, which also has not been previously reported.

Figure 2:
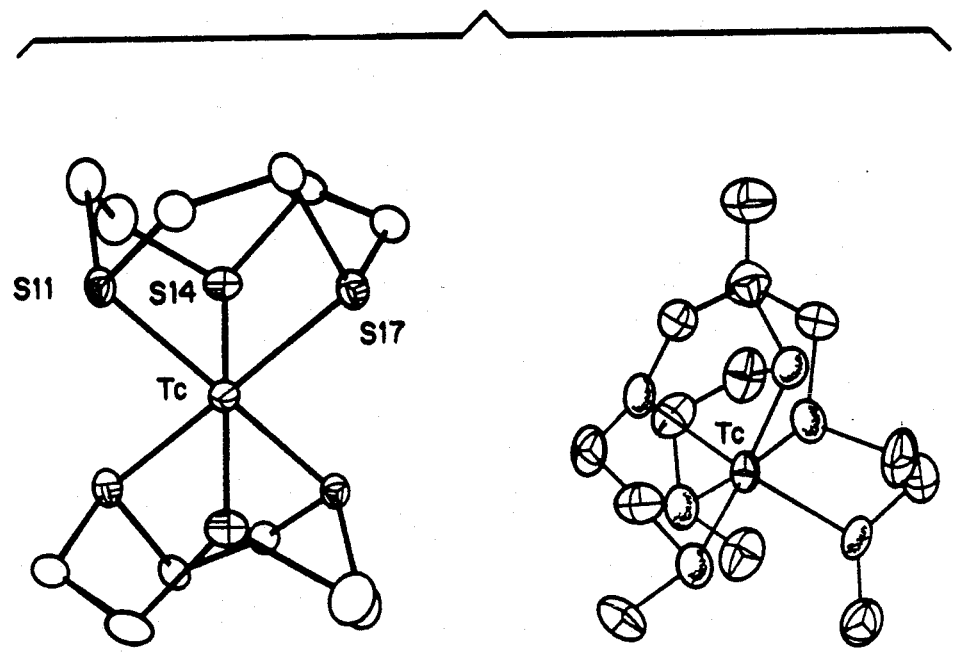

Analogy with the known coordination chemistry of these ligands suggests for them the structures shown in FIG. 2, namely [Tc(9S3)$_2$]$^{2+}$ and [TcL]$^{2+}$ respectively.

Biodistribution Data for [$^{99m}$Tc(9S3)$_2$]$^{n+}$ (n=1, 2)

[$^{99m}$Tc(9S3)$_2$]$^+$ was made by SnCl$_2$ reduction of [$^{99m}$Tc(9S3)$_2$]$^{2+}$. Biodistribution was determined in female CD mice at 1 h post injection given as mean %ID/g (S.D.) (N=2 except as indicated).

|  | [$^{99m}$Tc(9S3)$_2$]$^{2+}$ | | [$^{99m}$Tc(9S3)$_2$]$^{n+}$ | |
|---|---|---|---|---|
| blood | 1.53 | (0.23) | 1.33 | (0.43) |
| urine |  |  |  |  |
| feces | 1.38 | (0.54) |  |  |
| heart | 0.6 | (0.12) | 0.76 | (0.09) |
| lungs | 2.17 | (0.24) | 2.46 | (0.19) |
| thyroid | 1.11 | (N = 1) | 1.43 | (N = 1) |
| liver/gall bladder | 14.45 | (1.68) | 12.28 | (1.59) |
| stomach | 0.52 | (0.07) | 0.80 | (0.21) |
| spleen | 1.59 | (1.11) | 1.51 | (0.01) |
| gut/pancreas | 6.11 | (0.31) | 10.28 | (0.60) |
| kidney | 17.2 | (0.28) | 15.78 | (1.92) |
| bladder | 2.4 | (N = 1) | 1.40 | (0.04) |
| brain | 0.13 | (0.09) | 0.06 | (0.01) |
| muscle (thigh) | 0.35 | (0.14) | 0.25 | (0.06) |
| bone (femur) | 0.56 | (0.18) | 0.32 | (0.06) |
| adrenal | 0.58 | (N = 1) | 1.46 | (0.21) |
| % retained | >57, | >53 | >60, | >76 |

We claim:

1. A Technetium complex of a crown thioether having 3 to 6 donor sulphur atoms joined into a macrocyclic ring by ethylene or trimethylene groups.

2. A complex as claimed in claim 1 wherein the crown thioether is 1,4,7-trithiacyclononane.

3. A complex as claimed in claim 2 having the formula [TcL$_2$]$^+$ or [TcL$_2$]$^{2+}$ or [TcL$_2$]$^{3+}$ where L is the crown thioether.

4. A Technetium complex of a 1,1,1-substituted ethane in which each of the three substituents contains at least one sulphur atom having more than three donor sulphur atoms joined by ethylene or trimethylene groups.

5. A complex as claimed in claim 4, wherein the ligand is 1,1,1-tris(((2-methylthio)ethylthio)-methyl) ethane.

6. A complex as claimed in claim 5 having the formula [TcL]$^+$ or [TcL]$^{2+}$ or [TcL]$^{3+}$ where L is the ligand.

7. A complex as claimed in any one of claims 1 to 6, wherein the Technetium is Technetium-99m.

* * * * *